(12) United States Patent
Ross et al.

(10) Patent No.: US 8,740,784 B2
(45) Date of Patent: Jun. 3, 2014

(54) RIGIDIZABLE ENDOLUMINAL ACCESS DEVICE

(75) Inventors: Adam Ross, Prospect, CT (US); Gregg C. Krehel, Newtown, CT (US)

(73) Assignee: Covidien LP, Mansfield, MA (US)

( * ) Notice: Subject to any disclaimer, the term of this patent is extended or adjusted under 35 U.S.C. 154(b) by 1171 days.

(21) Appl. No.: 12/595,002

(22) PCT Filed: Apr. 16, 2008

(86) PCT No.: PCT/US2008/060394
§ 371 (c)(1),
(2), (4) Date: Oct. 7, 2009

(87) PCT Pub. No.: WO2008/130950
PCT Pub. Date: Oct. 30, 2008

(65) Prior Publication Data
US 2011/0166422 A1    Jul. 7, 2011

(51) Int. Cl.
*A61B 1/32* (2006.01)
(52) U.S. Cl.
USPC .......................................... 600/204
(58) Field of Classification Search
USPC ................ 606/201, 204; 227/176.1; 600/201, 600/204–206, 209, 210, 215, 216, 229
See application file for complete search history.

(56) References Cited

U.S. PATENT DOCUMENTS

| | | | |
|---|---|---|---|
| 5,759,151 A | 6/1998 | Sturges | |
| 5,826,776 A | 10/1998 | Schulze et al. | |
| 7,090,637 B2 | 8/2006 | Danitz et al. | |
| 7,169,130 B2 | 1/2007 | Exline et al. | |
| 2003/0229271 A1* | 12/2003 | Briscoe et al. | 600/229 |
| 2005/0137456 A1 | 6/2005 | Saadat et al. | |
| 2005/0273084 A1 | 12/2005 | Hinman et al. | |
| 2006/0189845 A1 | 8/2006 | Maahs et al. | |
| 2007/0005041 A1 | 1/2007 | Frassica et al. | |
| 2007/0185453 A1* | 8/2007 | Michael et al. | 604/164.01 |
| 2009/0192466 A1* | 7/2009 | Sniffin | 604/167.01 |

OTHER PUBLICATIONS

International Search Report for PCT/US08/060394 date of completion is Aug. 2, 2008 (2 pages).
European Search Report dated Apr. 9, 2013 from corresponding European Application No. EP 08745902.0. (6 pgs).

\* cited by examiner

*Primary Examiner* — Michael T Schaper
*Assistant Examiner* — Michael Araj (57) ABSTRACT

A rigidizable endoluminal access device includes a handle assembly 110, a flexible neck, a tip, and at least one lumen extending therethrough. Lumens are in fluid communication with entry ports located at the handle assembly and exit ports positioned on the tip. In one embodiment, entry ports and exit ports are angled with respect to one another. Lumens are configured to receive any suitable surgical instrument. The handle assembly includes an over-center toggle mechanism adapted to stiffen the flexible neck.

16 Claims, 14 Drawing Sheets

RIGIDIZABLE ENDOLUMINAL ACCESS DEVICE

CROSS-REFERENCE TO RELATED APPLICATIONS

This application is a National Stage Application of PCT/US2008/060394 under 35 USC §371(a), which claims priority of U.S. Provisional Patent Application Ser. No. 60/925,044 filed Apr. 17, 2007, the disclosures of each of the above-identified applications are hereby incorporated by reference in their entirety.

BACKGROUND

Endoluminal surgery encompass all surgical procedures that involve intentional instrument penetration into a lumen of a human body, such as the vascular lumens, the gastrointestinal lumens, or the air exchange lumens. These procedures generally entail diagnosis or treatment of diseases or debilitating conditions. Surgeons usually utilize a rigid or flexible tube, such as an endoscope, during endoluminal surgery. The tube is normally introduced into the human body through a body orifice, such as the mouth or rectum, or through an incision. Endoscopes, in particular, allow surgeons to view the target surgical site and may provide one or more working channels, or pathways, to the treatment site. During endoluminal surgical procedures, the surgeons steers or places the endoscope through the body until it reaches the intended site. Thereafter, the surgeon may perform the appropriate medical procedure.

TECHNICAL FIELD

The present disclosure relates to surgical instruments and methods. More particularly, the present disclosure relates to a rigidizable endoluminal access device.

SUMMARY

The present disclosure relates to a rigidizable endoluminal access device for providing access to a surgical site through a body lumen. The rigidizable endoluminal access device includes a handle, a neck operatively connected to the handle, a stiffening mechanism disposed in mechanical cooperation with the neck, and a lumen extending longitudinally along the access device. The neck has a flexible state and a rigid state. The stiffening mechanism is adapted to transform the neck between the flexible state and the rigid state. The access device may further include a seal positioned in the lumen for providing sealed passage to the surgical site.

In another embodiment, the rigidizable endoluminal access device includes a handle, a neck operatively connected to the handle, a stiffening mechanism disposed in mechanical cooperation with the neck, and a plurality of lumens extending longitudinally along the access device. The neck has a flexible state and a rigid state. The stiffening mechanism is adapted to transform the neck between the flexible state and the rigid state.

BRIEF DESCRIPTION OF THE DRAWINGS

Embodiments of the presently disclosed access device are described herein with reference to the accompanying drawings, wherein.

DETAILED DESCRIPTION OF THE EMBODIMENTS

Embodiments of the presently disclosed access device will now be described in detail with reference to the drawings wherein like reference numerals identify similar or identical elements. In the drawings and in the description which follows, the term "proximal," as is traditional, will refer to the end of the access device that is closest to the operator, while the term "distal" will refer to the end of the access device that is farthest from the operator. In the present disclosure, the words "a," "an," or "the" are to be taken to include both the singular and the plural. Similarly, any reference to plural items shall, where appropriate, include the singular.

The present disclosure relates to a rigidizable endoluminal access device for use in surgical procedures. The access device provides access to a working space inside a human body. Physicians can utilize the presently disclosed access device in many kinds of surgical procedures including, but not limited to, endoluminal, endoscopic and laparoscopic procedures. In addition, the access device of the present disclosure can be employed in combination with any suitable surgical instrument.

Figure 1:
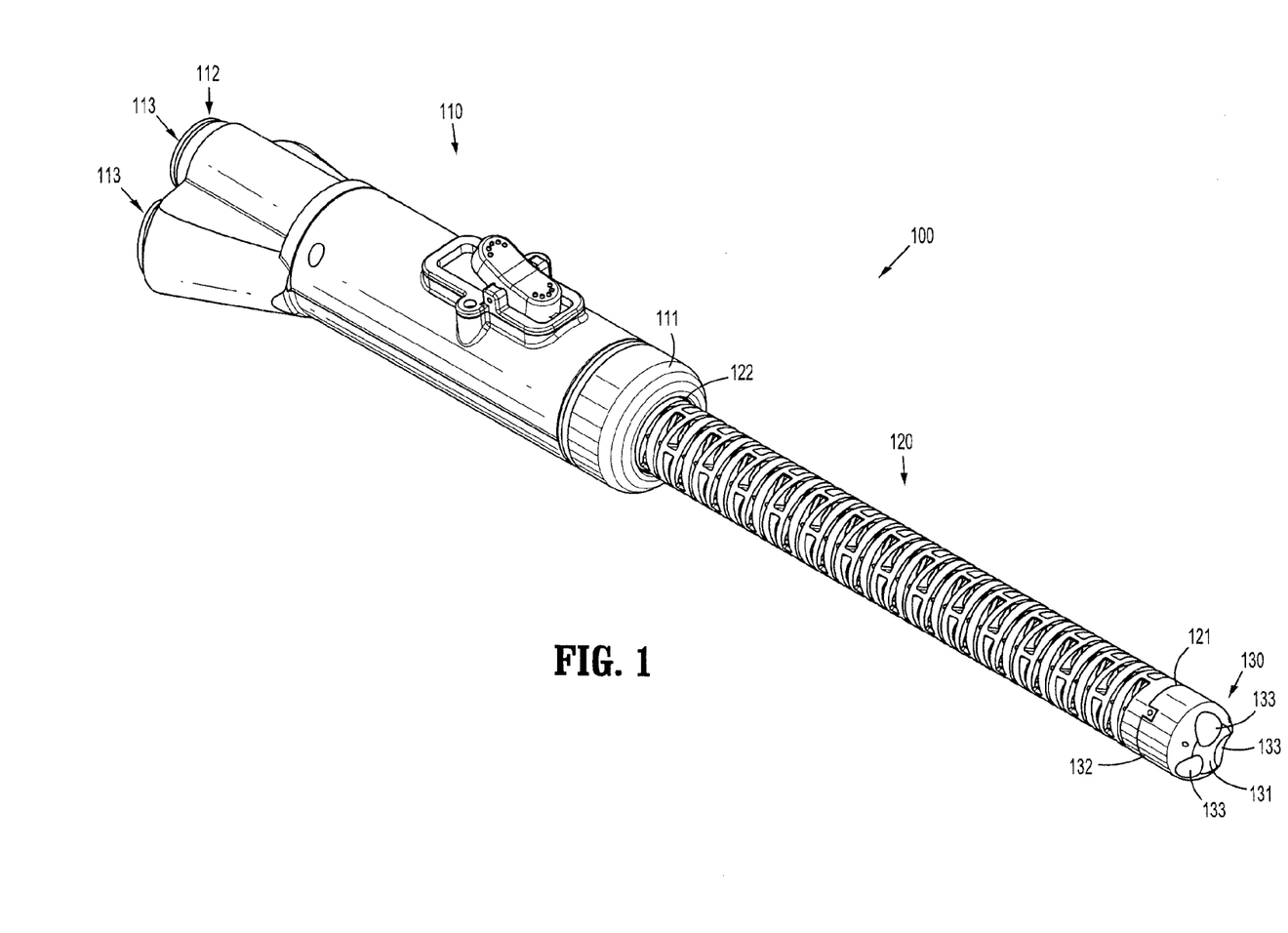
FIG. 1 is front perspective view of an access device according to an embodiment of the present disclosure.
Figure 2:
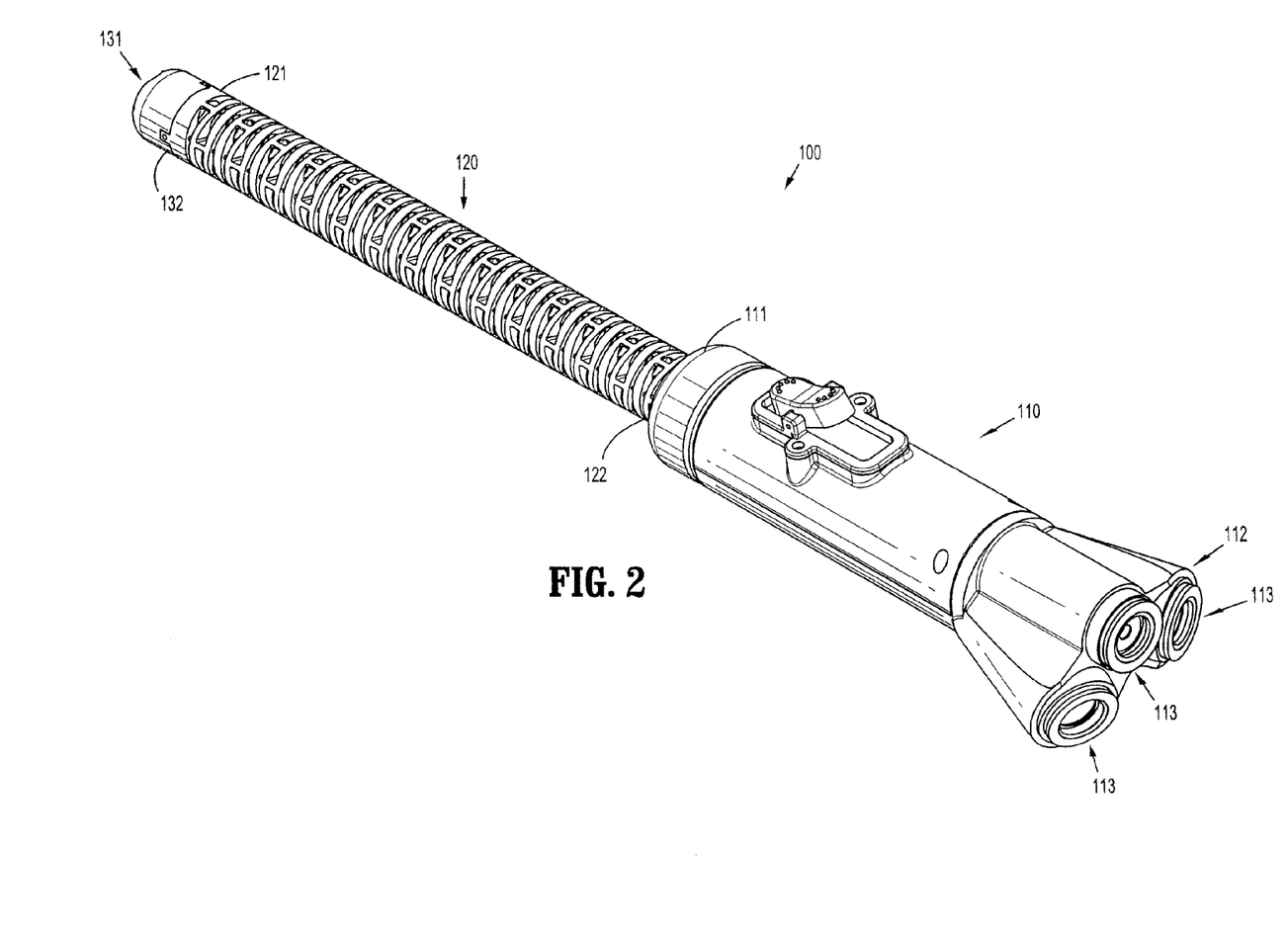
FIG. 2 is a rear perspective view of the access device of FIG. 1.

Referring initially to FIGS. 1-2, an access device is generally designated as reference numeral 100. Access device 100 includes a handle assembly 110, a flexible neck 120, and a tip 130. A distal end 111 of handle assembly 110 is secured to a proximal end 122 of flexible neck 120. In turn, a distal end 121 of flexible neck 120 is operatively connected to a proximal end 132 of tip 130. Accordingly, flexible neck 120 interconnects handle assembly 110 and tip 130.

Handle assembly 110 has at least one entry port 113 adapted to receive a surgical instrument. As seen in FIG. 2, an embodiment of the present disclosure includes a handle assembly 110 having three entry ports 113. In the depicted embodiment, three entry ports 113 are angled with respect to one another. The present disclosure, however, contemplates any suitable number of entry ports 113 positioned in different arrangements. For instance, handle assembly 110 can have two entry ports that are substantially parallel to each other.

Figure 10:
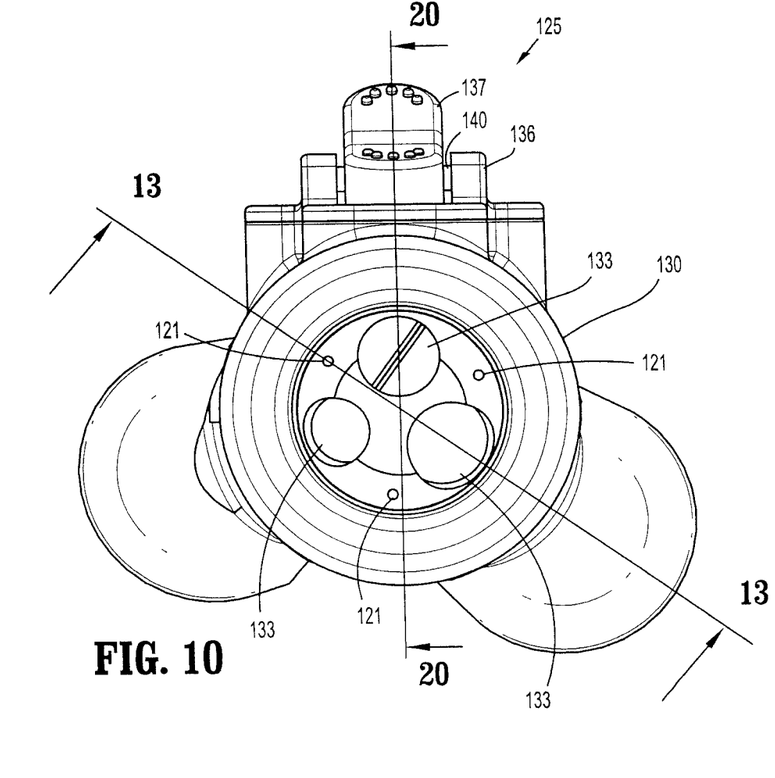
FIG. 10 is a front elevational view of the access device of FIG. 1.
Figure 17:
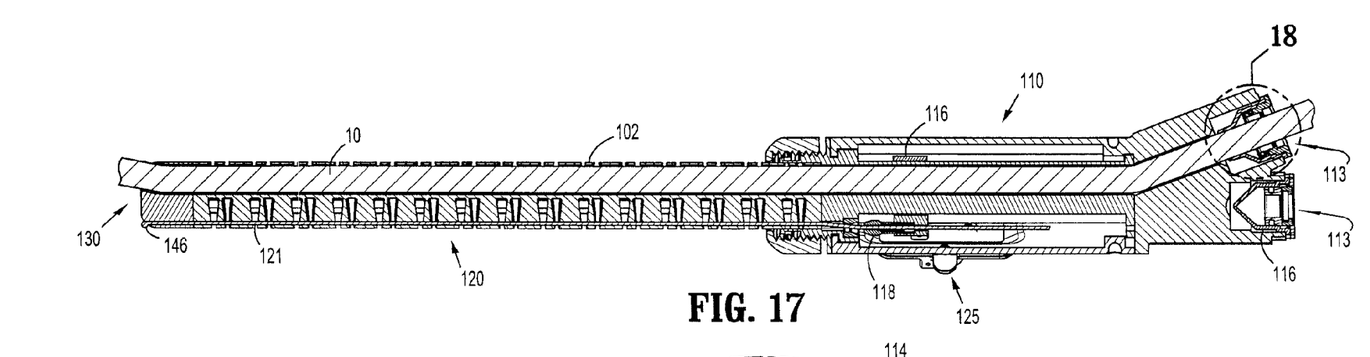
FIG. 17 is a side cross-sectional view of the access device of FIG. 1 with a surgical instrument inserted therethrough.

As discussed hereinabove, flexible neck 130 interconnects tip 130 and handle assembly 110. Tip 130 includes at least one exit port 133 configured to receive at least a portion of a surgical instrument. In one embodiment, tip 130 has three exit ports 133, as seen in FIG. 10. The illustrated exit ports 133 are angled with respect to one another, but the present disclosure envisions exit ports 133 having other kinds of spatial relationships. Each exit port 133 is in fluid communication with a corresponding entry port 113 through a lumen 102 that extends along the length of access device 100, as shown in FIG. 17. As it should be expected, access device 100 can have one or more lumens 102. Regardless of the quantity of lumens 102 in access device 100, each lumen 102 is adapted to receive a surgical instrument therethrough. The portion of lumens 102 that extend through flexible neck 120 can include a lining so that a surgical instrument can be inserted and extracted more easily. This lining can be made of a polymer.

Figure 3:
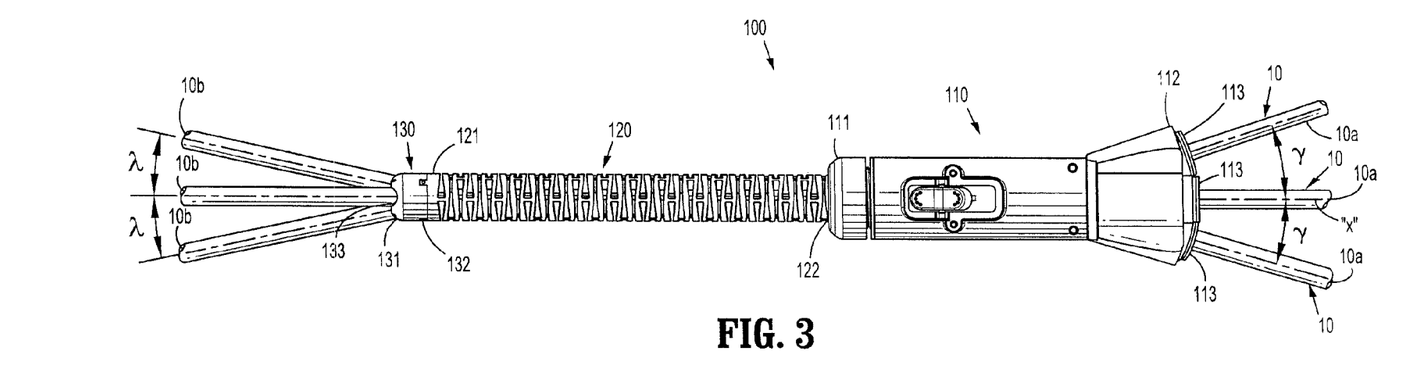
FIG. 3 is top view of the access device of FIG. 1.
Figure 4:
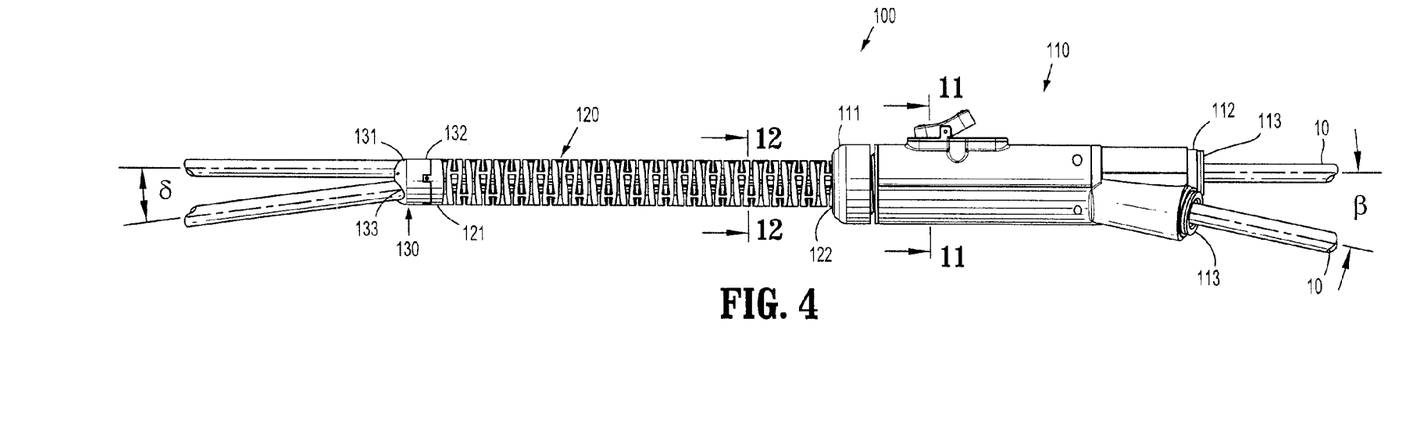
FIG. 4 is a side elevational view of the access device of FIG. 1.

Referring to FIGS. 3 and 4, an embodiment of access device 100 includes three lumens 102 connecting three angled entry ports 113 with three corresponding angled exit ports 133. Additionally, three surgical instruments 10 are disposed in lumens 102. Angled entry ports 113 facilitate insertion of surgical instruments 10 into access device 100 and can be laterally oriented at an angle γ of one another with respect to a longitudinal axis "X," as shown in FIG. 3. In addition, entry ports 113 can be oriented vertically with respect to one another at an angle β, as seen in FIG. 4. Similarly, angled exit ports 133 can be oriented vertically at an angle δ with respect to each other. Further, exit ports 133 can be oriented laterally at an angle λ with respect to longitudinal axis "X." Altogether, the arrangement of entry and exit ports 113, 133 improves triangulation of surgical instruments 10 upon exit into a working space. Thus, surgeons using access device 100 can efficiently locate a specific site within the designated working space.

Figure 5:
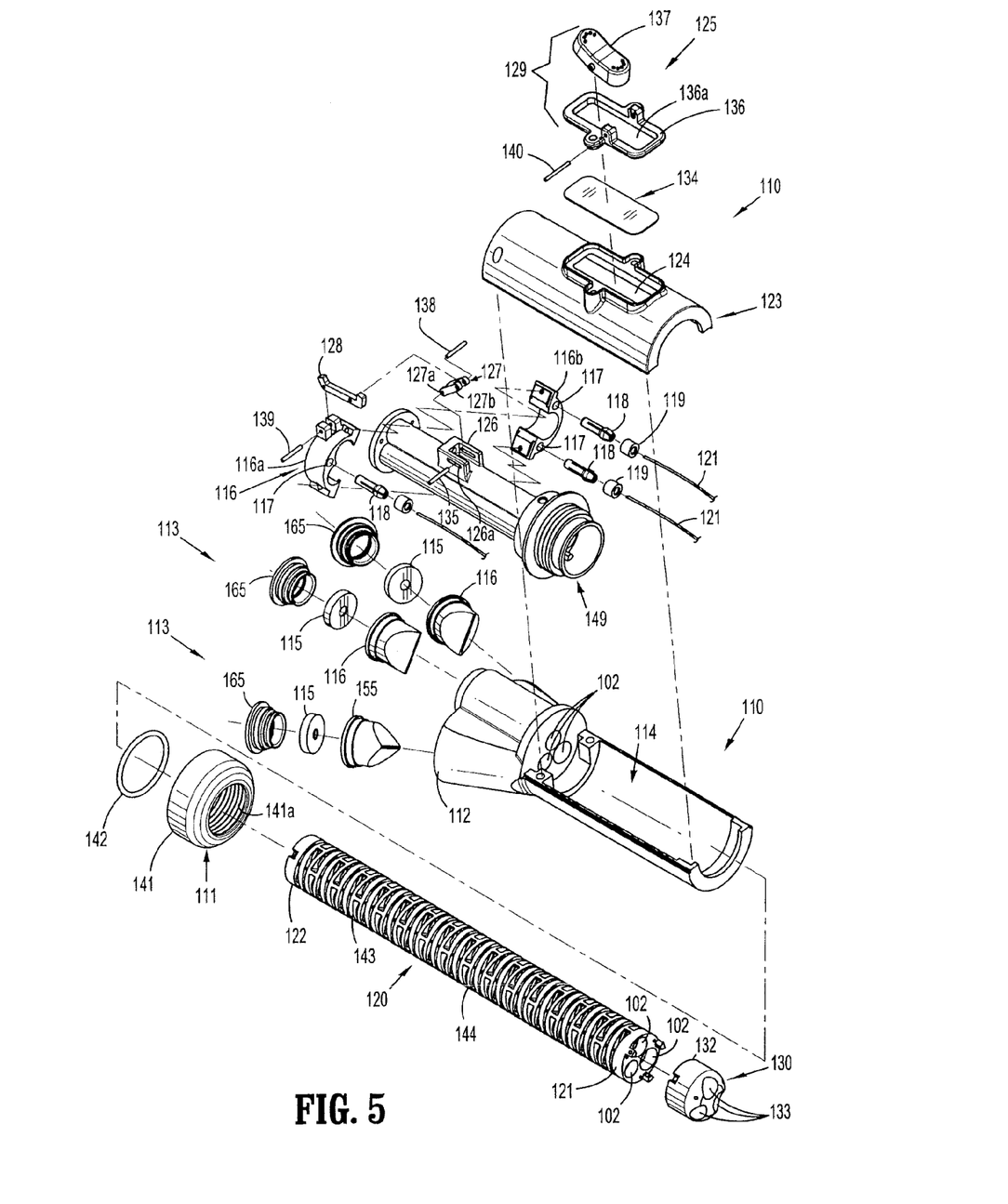
FIG. 5 is an exploded perspective view of the access device of FIG. 1.

Referring now to FIG. 5, access device 100 includes handle assembly 110 with at least one entry port 113 adapted to receive a surgical instrument. Each entry port 113 includes a cap 165, a first seal 115, and a second seal 155. First seal 115 lies on a distal end of cap 165 and encompasses at least a portion of cap 165. In one embodiment, first seal 115 is a septum seal. Those skilled in the art, however, will envision that first seal 114 can consist of any suitable seal. Second seal 155 surrounds at least a portion of first seal 115 and cap 165. In the drawings, second seal 155 is represented by a duckbill seal; nevertheless, second seal 155 can consist of any suitable seal capable of allowing flow in one direction while restricting flow in the opposite direction. In all, each entry port 113 is in fluid communication with at least one lumen 102.

Figures 6, 7:
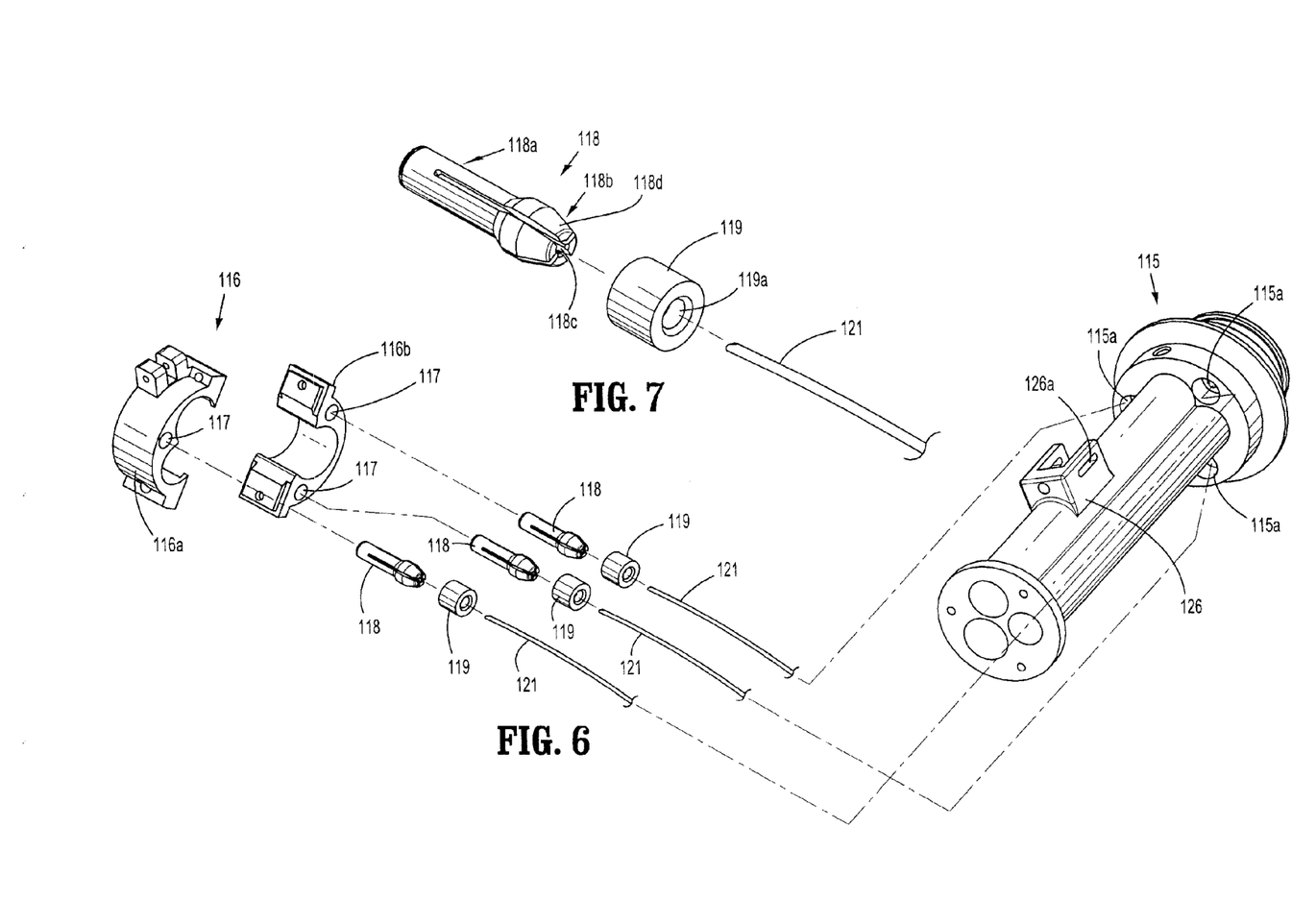
FIG. 6 is an exploded perspective view of some internal components of the access device of FIG. 1.
FIG. 7 is an exploded perspective view of a collet, a sleeve, and a portion of a cable of the access device of FIG. 1.

Handle assembly 110 contains a recess 114 configured to retain several internal components of access device 100. For instance, a tubular member 149 partially occupies recess 114 and forms at least a portion of lumens 102. One having ordinary skills in the art will recognize that tubular member 149 could form a single lumen 102. Tubular member 149 additionally includes at least one bore 115a on a distal portion thereof, as seen in FIG. 6. Bores 115a are adapted to receive sleeves 119. Recess 114 also contains a ring 116 slidably positioned around tubular member 149. Ring 116 includes at least one bore 117 adapted to receive a collet 118.

Figure 15:
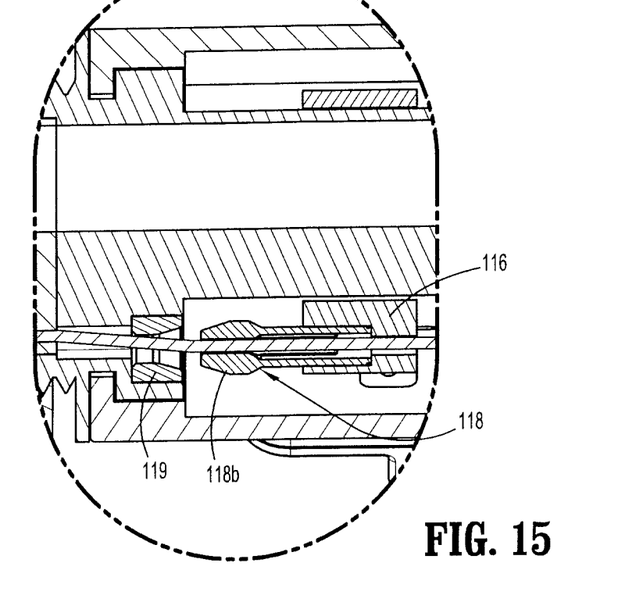
FIG. 15 is a side sectional view of a portion of the access device of FIG. 1; taken around section 15 of FIG. 13.
Figure 16:
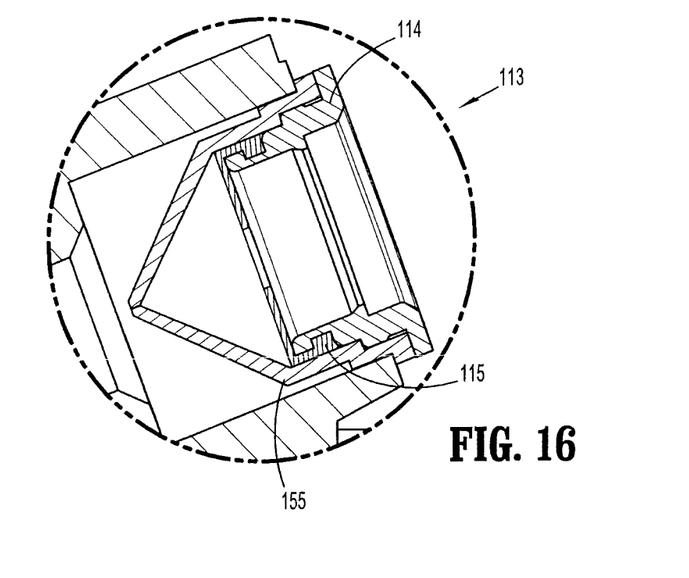
FIG. 16 is a side sectional view of a portion of the access device of FIG. 1, taken around section 16 of FIG. 13.

Referring to FIGS. 6 and 7, in one embodiment, ring 116 is composed by two matching parts 116a, 116b, each operatively secured to one another. Each matching part 116a, 116b may have one or more bores 117 adapted to receive collets 118. Collets 118 have a tubular structure 118a, a camming structure 118b, and a bore 118c extending therethrough. Camming structure 118b includes a plurality of collapsible fingers 118d. Bores 118c are configured to receive at least a portion of cable 121, as depicted in FIG. 15. A spring may be added over each collet 118 to bias ring 116 proximally.

Figures 8, 9:
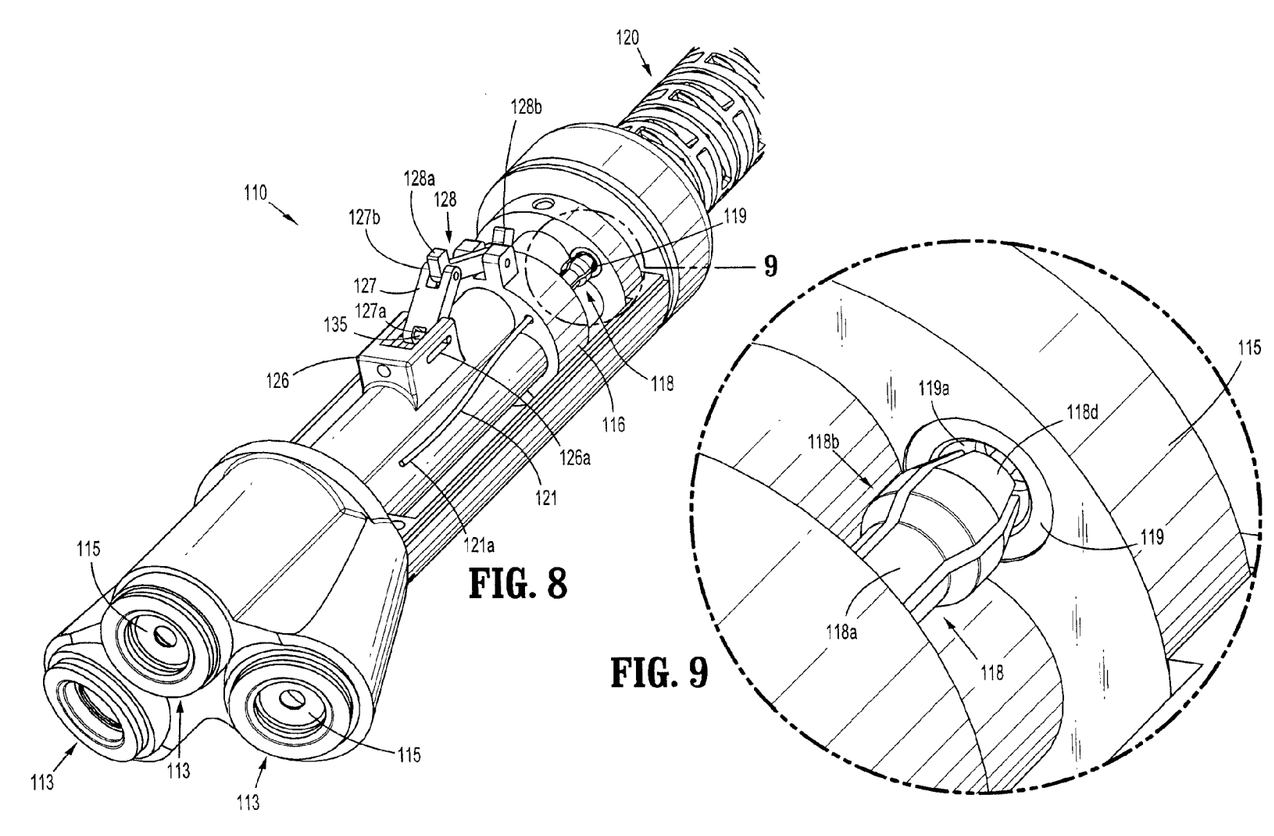
FIG. 8 is a rear perspective view of a proximal portion of the access device of FIG. 1 with a hatch removed to show some internal components.
FIG. 9 is a perspective sectional view of a portion of the access device of FIG. 1, taken around section 9 of FIG. 8.

Referring to FIGS. 8 and 9, recess 114 also houses at least a portion of at least one cable 121. In an embodiment, access device 100 includes three cables 121. Each cable 121 passes through bore 118c of collet 118 and a bore 119a of sleeve 119 and has a proximal end 121a and distal end 121b (see FIG. 14). The proximal ends 121a of cables 121 can optionally free float within recess 114. Alternatively, springs can be positioned at the proximal ends 121a of cables 121 to provide a degree of stiffness to cables 121. Bore 119a of sleeve 119 is adapted to receive the camming structure 118b of collet 118. The internal surfaces defining bore 119a of sleeve 119 are configured to compress the camming structure 118b of collet 118. Handle assembly 110 includes at least one sleeve 119 positioned in bore 115a of tubular member 149, as shown in FIG. 6. In the illustrated embodiment, handle assembly 110 has a tubular member 149 with three bores 115a positioned at the distal portion thereof. Sleeves 119 are disposed in bores 115a of tubular member 149.

Returning to FIG. 5, handle assembly 110 includes a hatch 123 configured to cover recess 114. Hatch 123 has an opening 124 adapted to receive at least a portion of an over-center toggle mechanism 125. Over-center toggle mechanism 125 controls the axial motion of ring 116 and includes a base 126 disposed on tubular member 149, a first link 127, a second link 128, a toggle member 129, and a toggle seal 134. A proximal end 127a of first link 127 is slidably and pivotably connected to base 126. In an embodiment, a first pin 135 slidably and pivotably couples the proximal end 127a of first link 127 to base 126. Base 126 has at least one longitudinal slot 126a configured to receive first pin 135.

A distal end 127b of first link 127 is pivotably secured to a proximal end 128a of second link 128. A second pin 138 may pivotably connect distal end 127 of first link 127 and proximal end 128a of second link 128. A distal end 128b of second link 128 is pivotably fixed to ring 116, as illustrated in FIG. 8. A third pin 139 can pivotably secure distal end 128b of second link 128 and ring 116.

Over-center toggle mechanism 125 also includes a toggle seal 134 designed to cover opening 124 of hatch 123. Toggle seal 134 can be a flexible airtight seal. Toggle member 129 is positioned over toggle seal 134 and includes a toggle support member 136 and a button 137. Support member 136 is disposed on and attached to hatch 123 and includes an opening 136a adapted to receive at least a portion of first and second links 127, 128. Button 137 is pivotably attached to support member 136. In an embodiment, a toggle pin 140 pivotably connects button 137 and support member 136, as shown in FIG. 5. During use, an operator can actuate over-center toggle mechanism 125 to slide (distally or proximally) ring 116 along at least a portion of the length of tubular member 149. When ring 116 is moved distally, collet 118 translates distally and positions its camming structure 118b into sleeve 119. At this point, sleeves 119 exert pressure on camming structure 118b and compress fingers 118d. The compression of fingers 118d of camming structure 118b axially locks cables 121 into position.

As discussed hereinabove, the distal end 111 of handle assembly 110 is secured to a proximal end 122 of flexible neck 120. Distal end 111 includes a cap 141 and a third seal 142 disposed therein. Cap 141 has a bore 141 a extending therethrough and adapted to receive flexible neck 120. Bore 141a may be internally threaded.

A proximal end 122 of flexible neck 120 is operatively secured to distal end 111 of handle assembly 110. Flexible neck 120 is formed by a plurality of ribs 143 operatively coupled to one another. A series of slits 144 separate ribs 143 from each other. In addition to a one-piece flexible segment, flexible neck 120 can alternatively be formed from a series of interconnecting segments. Regardless of the specific structure of flexible neck 120, a flexible sheet can surround flexible neck 120 to maintain a seal for insufflation. This flexible sheet can be made of a polymer.

Figure 11:
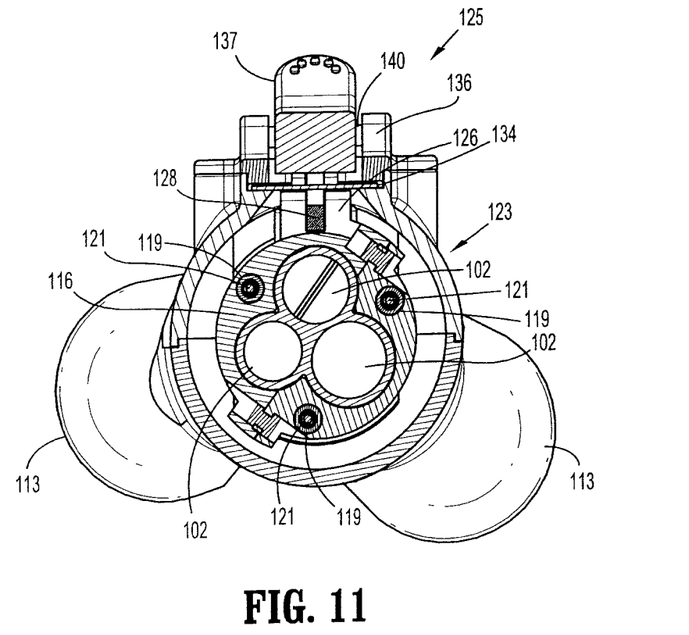
FIG. 11 is a front cross-sectional view of the access device of FIG. 1, taken along section lines 11-11 of FIG. 4.
Figure 12:
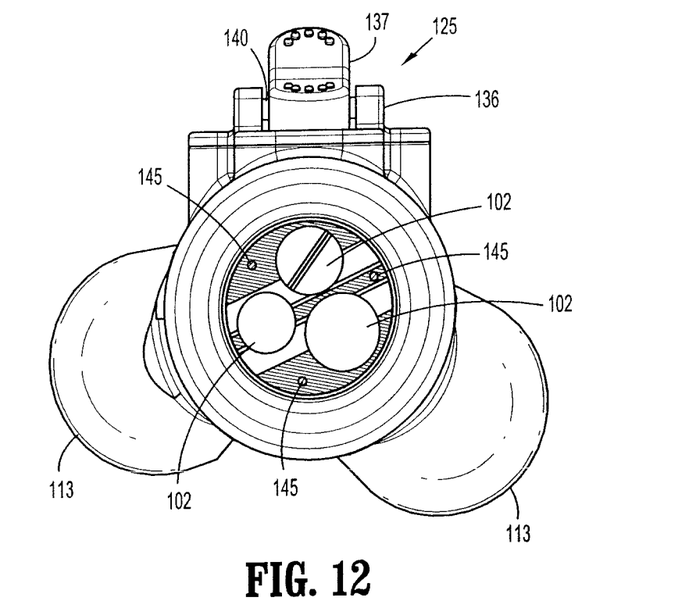
FIG. 12 is a front cross-sectional view of the access device of FIG. 1, taken along section lines 12-12 of FIG. 4.

As seen in FIGS. 11 and 12, flexible neck 120 includes at least one bore 145 extending therethrough. The depicted embodiment shows a flexible neck 12 having three bores 145 with three cables 121 inserted therethrough. Each bore 145 is adapted to receive a cable 121. Additionally, at least one lumen 102 extends through the length of flexible neck 120.

Cables 121 extend along the length of flexible neck 120 and into tip 130. Although flexible, cables 121 have certain degree of stiffness. For example, in one embodiment, cables 121 are made of wires. During operation, surgeons can physically bend flexible neck 120 to any direction prior to introducing access device 100 into a body lumen. Alternatively, physicians may insert access device 100 into a body lumen and flexible neck 120 orientation will adjust according to the shape of the lumen. Flexible neck 130 can effectively bend in any direction. When flexible neck 120 is articulated, adjacent ribs approximate one another in one side and separate in the other side.

Figure 13:
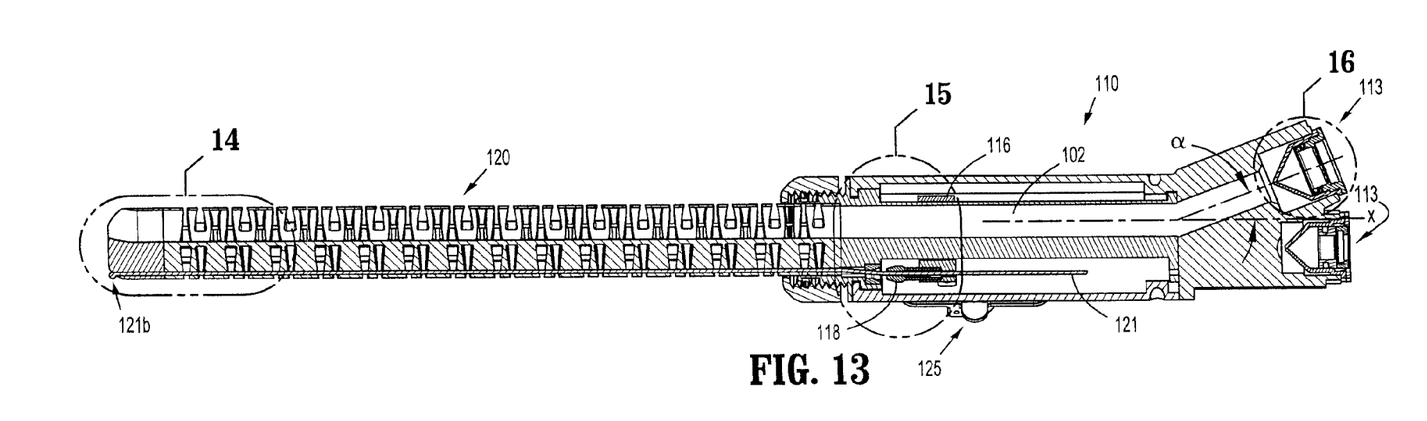
FIG. 13 is a side cross-sectional view of the access device of FIG. 1, taken along section lines 13-13 of FIG. 10.
Figure 14:
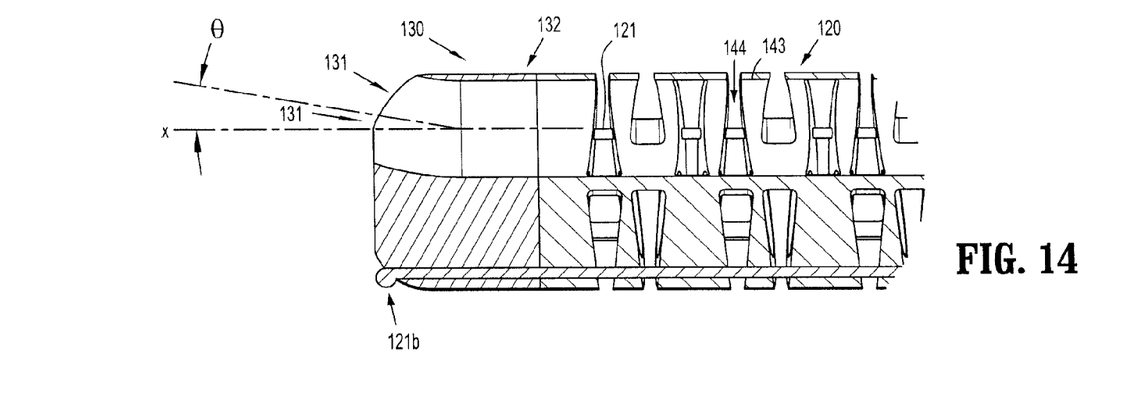
FIG. 14 is side sectional view of a portion of the access device of FIG. 1, taken around section 14 of FIG. 13.

With reference to FIGS. 13 and 14, distal ends 121b of cables 121 are operatively attached to a distal end 131 of tip 130. Those skilled in the art will recognize that distal ends 121b of cables 121 can be secured to distal end 131 of tip 130 with a knot, a soldered-on-ball joint, a solder blob or any other suitable fitting. In one embodiment, the distal ends of cables 121 have swaged tubular fittings. These tubular fittings are slightly larger than the diameter of bores 145 and operatively fix the distal ends 131 of tip 130 to the distal ends 121b of cables 121. To secure these fittings to the distal ends 131 of tip 130, the fittings can be pressed into the proximal end 132 of tip 130.

As discussed above, tip 130 has at least one exit port 133 in fluid communication with lumen 102 and entry port 113, as seen in FIG. 10. At least one exit port 133 can be oriented at an angle θ with respect to a longitudinal axis "X." Similarly, entry port 113 can be oriented at an angle α with respect to longitudinal axis "X."

With reference to FIGS. 13-16, in operation, ring 116 is initially in an unlocked position and the camming structure 118b of collet 118 is positioned in a neutral position outside of sleeve 119. Additionally, a portion of the lumen 102 that extends through the length of flexible neck 120 is collapsed.

Figure 18:
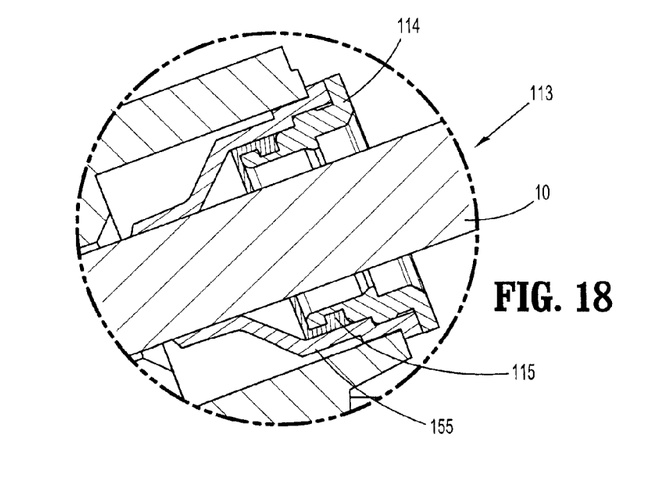
FIG. 18 is a side sectional view of a portion of the access device of FIG. 1, taken around section 18 of FIG. 17.
Figure 19:
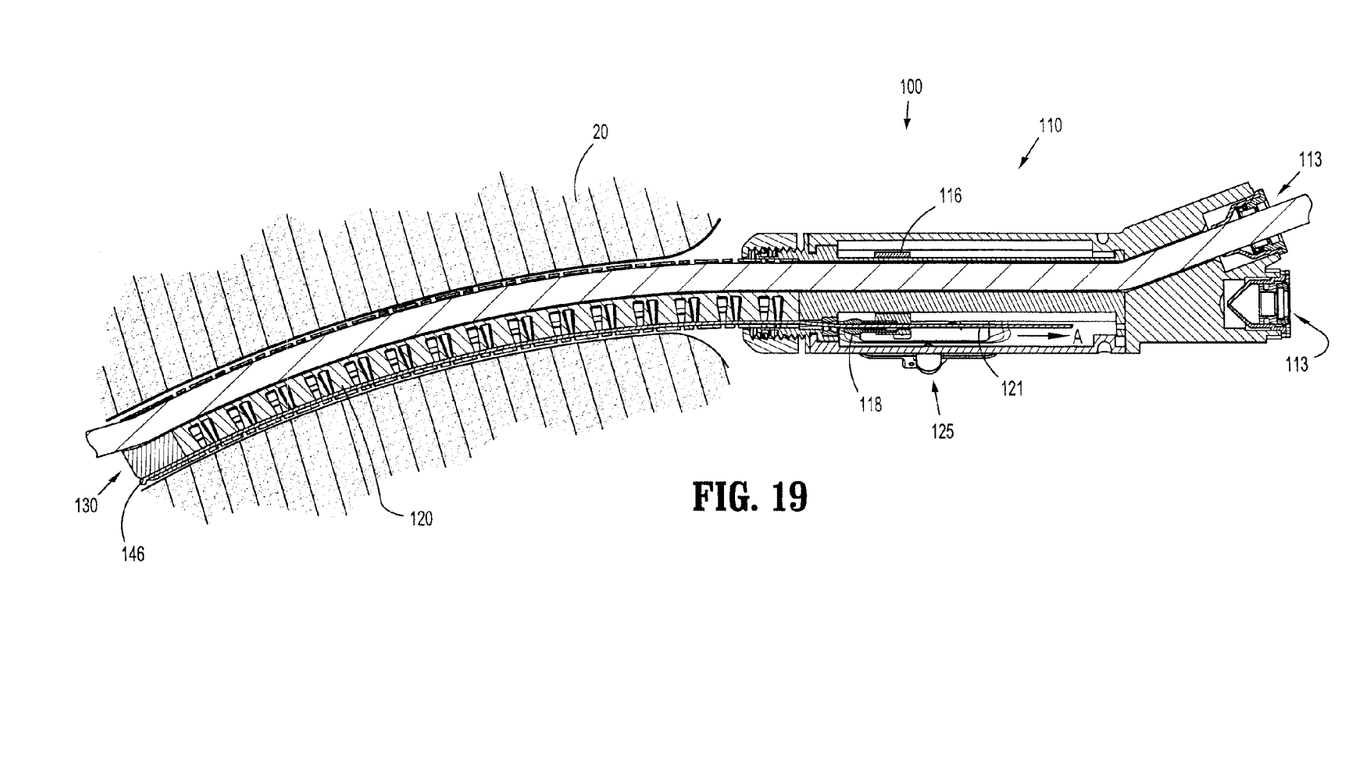
FIG. 19 is a side cross-sectional view of the access device and surgical instrument of FIG. 18 inserted through a body lumen.

Referring now to FIGS. 17 and 18, a surgeon may introduce any suitable instrument through lumen 102. Surgical instrument 10 extends throughout the length of access device 100. The portion of the lumen 102 positioned in flexible neck 120 expands when surgical instrument 10 is positioned therein, as seen in FIG. 17. At any time during the surgical procedure, the user may introduce access device 100 through a body lumen 20, as illustrated in FIG. 19. At this point, flexible neck 120 will bend to conform to the orientation and shape of a body lumen 20. While flexible neck 120 articulates, cables 121 translates through collet 118 and flexible neck 120, as indicated by arrow "A."

Figures 20, 21:
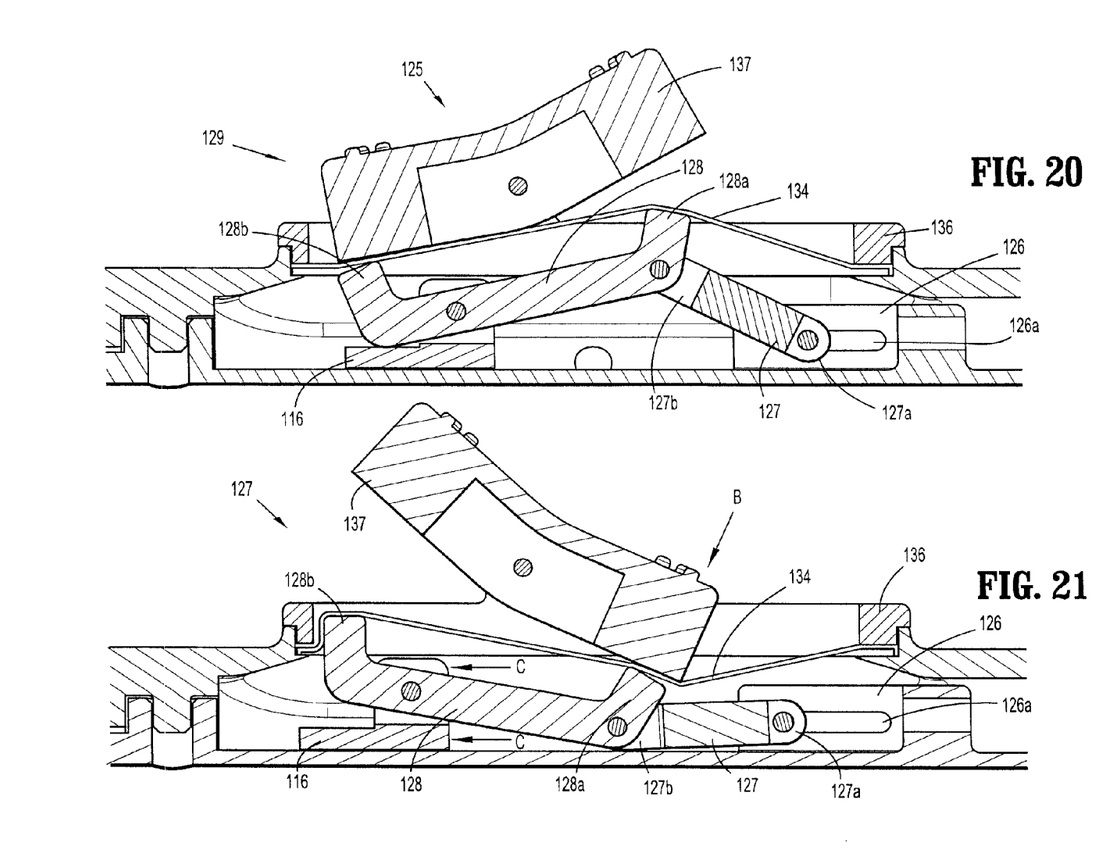
FIG. 20 is an over-center toggle mechanism of the access device of FIG. 1 in an unlocked position.
FIG. 21 is an over-center toggle mechanism of the access device of FIG. 1, in a locked position.
Figure 22:
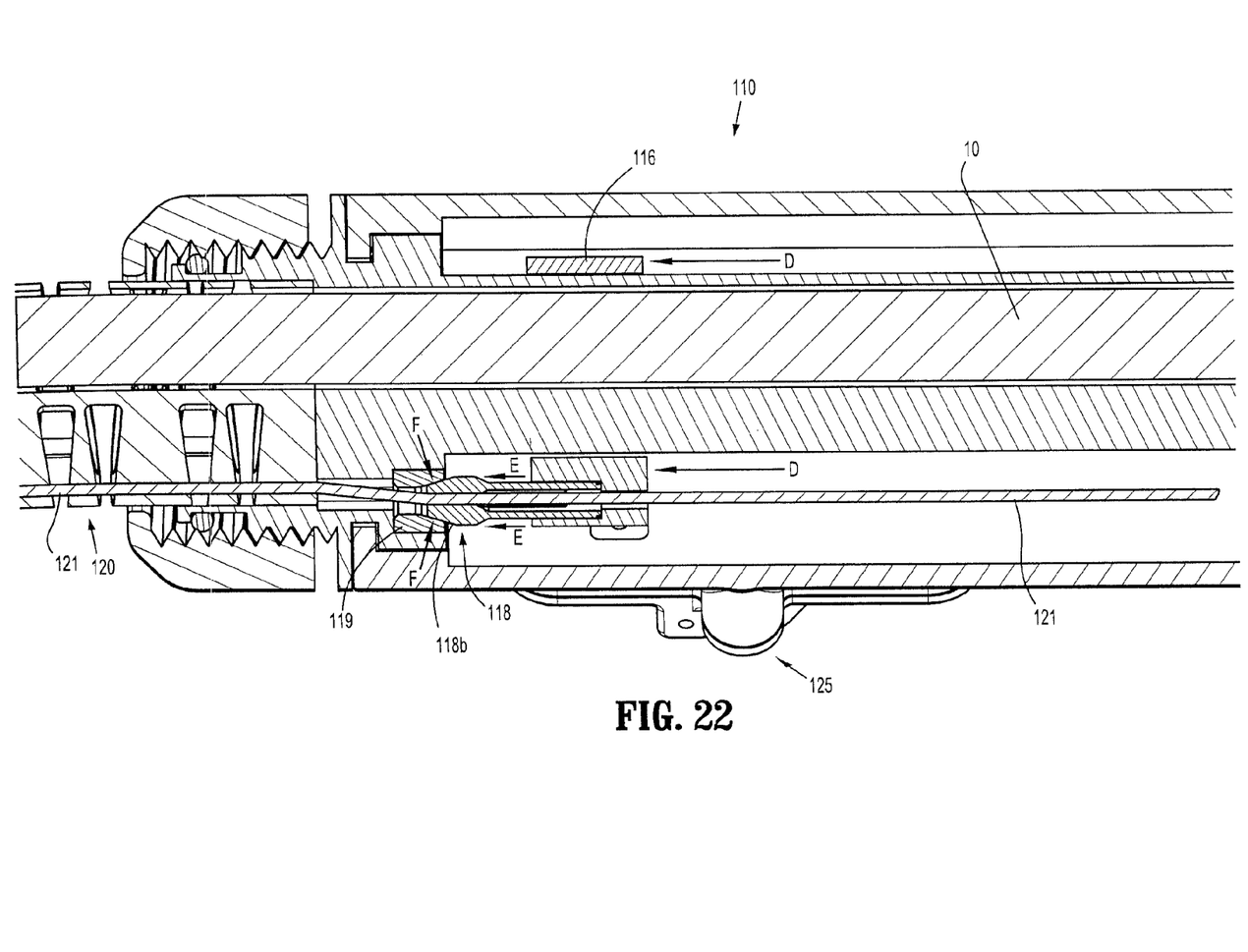
FIG. 22 is a side cross-sectional view of a portion of the access device of FIG. 1.

After access device 100 and surgical instrument are located in the desired surgical site, the operator may stiffen flexible neck 120. The user can stiffen flexible neck 120 by switching over-center toggle mechanism 125 from an unlocked position to a locked position. In an unlocked position, button 137 is in contact with the distal end 128b of second link 128, as seen in FIG. 20. Also, the proximal end 128a of second link 128 and the distal end 127b of second link 127 are inclined upwardly. To place over-center toggle mechanism 125 in the locked position, the user must moves button 137 in the direction indicated by arrow "B," as shown in FIG. 21. When the operator moves button 137, the proximal end 128a of second link 128 and the distal end 127b of first link 127 descend, causing the first and second links 127, 128 to slide distally. As first and second links 127, 128 translate distally, ring 116 moves distally in the direction indicated by arrows "C." While ring 116 slides along tubular member 149, collet 118 moves distally towards sleeve 119 in the direction indicated by arrows "E," as depicted in FIG. 22. The axial motion of collet 118 will eventually position its camming structure 118b inside sleeve 119. When camming structure 118b is located within sleeve 119, fingers 118d of camming structure 118b collapse due to the pressure exerted by sleeve 119 in the direction indicated by arrows "F." The pressure applied on camming structure 118b compresses fingers 118b and locks cable 121 into position, thereby stiffening flexible neck 120.

It will be understood that various modifications can be made to the embodiments disclosed herein. Therefore, the above description should not be construed as limiting, but merely as exemplifications of embodiments. Those skilled in the art will envision other modifications within the scope and spirit of the present disclosure.

What is claimed is:

1. A rigidizable endoluminal access device, comprising:
   a handle;
   a neck operatively connected to the handle, the neck having a flexible state and a rigid state;
   a stiffening mechanism disposed in mechanical cooperation with the neck, the stiffening mechanism including a cable extending along at least a portion of the neck and a collet having a bore adapted to slidably receive the cable, the stiffening mechanism configured to selectively tension and loosen the cable, thereby transforming the neck between the flexible state and the rigid state; and
   a lumen extending longitudinally along the access device, wherein the lumen is configured to receive a surgical instrument therethrough, wherein the collet includes a collapsible portion configured to substantially hinder sliding movement of the cable through the collet when the collapsible portion is compressed against the cable.

2. The rigidizable endoluminal access device according to claim 1, further comprising a seal positioned in the lumen for providing sealed passage to a surgical site.

3. The rigidizable endoluminal access device according to claim 2, wherein the seal is a duckbill seal.

4. The rigidizable endoluminal access device according to claim 1, wherein the lumen extends from a proximal end to a distal end of the access device.

5. The rigidizable endoluminal access device according to claim 1, wherein the stiffening mechanism includes a sleeve adapted to compress the collapsible portion of the collet against the cable when at least a section of the collapsible portion is placed within the sleeve.

6. The rigidizable endoluminal access device according to claim 5, wherein the stiffening mechanism includes a ring operatively coupled to the collet, the ring being configured to move the collapsible portion of the collet toward the sleeve.

7. The rigidizable endoluminal access device according to claim 6, further comprising a tubular member positioned within the handle, wherein the ring is slidably positioned around the tubular member.

8. The rigidizable endoluminal access device according to claim 6, further including a toggle mechanism operatively connected to the ring, wherein the ring moves longitudinally upon actuation of the toggle mechanism.

9. The rigidizable endoluminal access device according to claim 1, further including a toggle mechanism operatively connected to the stiffening mechanism, the toggle mechanism configured to actuate the stiffening mechanism.

10. The rigidizable endoluminal access device according to claim 1, wherein the lumen has an expandable portion adapted to expand upon insertion of the surgical instrument therethrough.

11. The rigidizable endoluminal access device according to claim 1, wherein a portion of the lumen includes a liner to facilitate insertion and removal of the surgical instrument therethrough.

12. A rigidizable endoluminal access device, comprising:
a handle;
a neck operatively coupled to the handle, the neck having a flexible state and a rigid state;
a stiffening mechanism disposed in mechanical cooperation with the neck, the stiffening mechanism including a cable extending along at least a portion of the neck and a collet having a bore adapted to slidably receive the cable, the collet including a collapsible portion configured to substantially hinder sliding movement of the cable through the collet when the collapsible portion of the collet is compressed against the cable; and
a plurality of lumens extending along the access device wherein each lumen has a collapsible portion adapted to expand upon insertion of a surgical instrument therethrough, wherein the stiffening mechanism is configured to selectively tension the cable thereby transforming the neck from the flexible state to the rigid state, and to selectively loosen the cable, thereby transforming the neck from the rigid state to the flexible state.

13. The rigidizable endoluminal access device according to claim 12, further comprising a seal positioned in at least one lumen of the plurality of lumens, wherein the seal is adapted to provide a sealed passage to a surgical site.

14. The rigidizable endoluminal access device according to claim 13, wherein the seal is a duckbill seal.

15. The rigidizable endoluminal access device according to claim 12, wherein at least one lumen of the plurality of lumens extends from a proximal end to a distal end of the access device.

16. The rigidizable endoluminal access device according to claim 12, wherein the stiffening member includes a sleeve adapted to compress the collapsible portion of the collet against the cable when at least a section of the collapsible portion is placed within the sleeve.

* * * * *